US005250079A

United States Patent [19]

Baumann

[11] Patent Number: 5,250,079

[45] Date of Patent: Oct. 5, 1993

[54] PROCESS FOR THE TREATMENT OF POLYAMIDE OR LEATHER SUBSTRATES WITH SULPHO GROUP-CONTAINING AROMATIC COMPOUNDS, COMPOSITIONS CONTAINING SUCH COMPOUNDS AND THEIR PRODUCTION

[75] Inventor: Hans-Peter Baumann, Ettingen, Switzerland

[73] Assignee: Sandoz Ltd., Basle, Switzerland

[21] Appl. No.: 926,878

[22] Filed: Aug. 7, 1992

Related U.S. Application Data

[63] Continuation of Ser. No. 652,812, Feb. 8, 1991, abandoned, which is a continuation-in-part of Ser. No. 572,520, Aug. 23, 1990, Pat. No. 5,207,802.

[30] Foreign Application Priority Data

| | | | |
|---|---|---|---|
| Aug. 25, 1989 | [DE] | Fed. Rep. of Germany | 3928170 |
| Feb. 10, 1990 | [DE] | Fed. Rep. of Germany | 4004101 |
| Aug. 20, 1990 | [DE] | Fed. Rep. of Germany | 4026255 |

[51] Int. Cl.$^5$ ...................... C14C 3/20; C07C 309/36; D06M 101/02; D06P 3/04

[52] U.S. Cl. ........................................... 8/557; 8/436; 8/531; 8/589; 8/648; 8/680; 8/94.19 R; 8/94.21; 8/92.4; 252/8.6; 252/8.7

[58] Field of Search .................... 8/589, 436, 94.19 R, 8/94.21, 557; 252/8.7

[56] References Cited

U.S. PATENT DOCUMENTS

| | | | |
|---|---|---|---|
| 4,202,838 | 5/1980 | Lauton et al. | 8/589 |
| 4,217,103 | 8/1980 | Wolf et al. | 8/665 |
| 4,341,526 | 7/1982 | Kuehni et al. | 8/610 |
| 4,465,492 | 8/1984 | Putzar | 8/589 |

*Primary Examiner*—A. Lionel Clingman
*Attorney, Agent, or Firm*—Robert S. Honor; Richard E. Vila; Thomas C. Doyle

[57] ABSTRACT

A process for the treatment of fibrous material from aqueous medium in the presence of an application assistant (P) comprising components (a) and (b), in particular for nitrogen-containing substrates; the compositions (P), ($P_1$) and ($P_2$) and compositions comprising (P) and anionic dye or optical brightener.

35 Claims, No Drawings

PROCESS FOR THE TREATMENT OF POLYAMIDE OR LEATHER SUBSTRATES WITH SULPHO GROUP-CONTAINING AROMATIC COMPOUNDS, COMPOSITIONS CONTAINING SUCH COMPOUNDS AND THEIR PRODUCTION

This is a continuation of application Ser. No. 07/652,812, filed Feb. 8, 1991, now abandoned, which in turn is a continuation-in-part of application Ser. No. 07/572,520, filed Aug. 23, 1990, now U.S. Pat. No. 5,207,802 issue date May 4, 1993.

It has been found that mixtures of defined sulphonated aromatic compounds (a) and (b), as defined below, are valuable application assistants of high lightfastness for the treatment of fibrous materials from aqueous medium, displaying outstanding levelling properties, in particular in the dyeing or optical brightening of nitrogen-containing fibrous materials or in the tanning, retanning or fat-liquoring of leather.

The invention relates to the treatment of fibrous material from aqueous medium in the presence of said mixtures resp. compositions as application assistants and to certain compositions and their production.

The invention thus provides a process for the treatment of fibrous material from aqueous medium in the presence of an application assistant, wherein the application assistant is a composition (P) comprising (a) a sulphonation product of a compound of formula

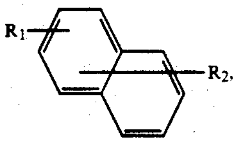

(I)

in which $R_1$ signifies $C_{1-4}$-alkyl and $R_2$ signifies hydrogen or $C_{1-4}$-alkyl, or of a mixture of compounds of formula (I) and (b) a sulphonation product of a compound of formula

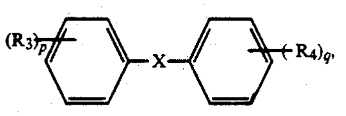

(II)

in which each of $R_3$ and $R_4$, independently, signifies $C_{1-4}$-alkyl, X signifies oxygen, sulphur or the direct bond and each of p and q, independently, signifies 0, 1 or 2, or of a mixture of compounds of formula (II)

optionally at least partially in salt form.

As alkyl groups with 1–4 carbon atoms in the significance of $R_1$, $R_2$, $R_3$ and $R_4$ all of the possible representatives come into consideration, namely methyl, ethyl, n-propyl, isopropyl, n-butyl, isobutyl, sec.butyl and t.butyl.

The number of the total of carbon atoms in $R_1+R_2$ amounts advantageously at least to 2, preferably at least to 3, in particular at least to 4. Preferably $R_2$ signifies $C_{1-4}$-alkyl. If $R_2$ signifies $C_{1-4}$-alkyl, the symbols $R_1$ and $R_2$ may have the same significance or different significances; preferably they have the same significance. Among the alkyl radicals in the significance of $R_1$ and $R_2$ the higher molecular ones are preferred, in particular $C_{3-4}$-alkyl, namely propyl and butyl of which the branched groups are particularly preferred, before all isopropyl. The alkyl radical $R_1$ may be in any of the positions α and β; if $R_2$ signifies $C_{1-4}$-alkyl also this radical may be in any of the positions α and β or α' and β'. Among the dialkyl substituted naphthalenes of formula (I) all possible positional isomers come into consideration, in particular the corresponding 1,3-, 1,4-, 1,5-, 1,6-, 1,7-, 2,6- and 2,7-dialkyl substituted naphthalenes. There may be employed single compounds or mixtures, advantageously technical isomeric mixtures.

The symbol X signifies preferably the direct bond or oxygen.

If p and/or q signify 1 or 2 the respective alkyl groups may be in any of the positions ortho, meta and para to X. As compounds of formula (II) in which only one of p and q is 1, the other signifying 0, there may be mentioned the corresponding 2-, 3- or 4-alkyl, principally -methyl-diphenylether or 2-, 3- or 4-isopropylbiphenyl and further technical mixtures of these compounds. Of the compounds in which each of p and q signifies 1 there may be mentioned the single positional isomers, 2,2', 2,3', 2,4', 3,3', 3,4' and 4,4', as well as mixtures in particular technical mixtures of such isomers; among these diisopropylbiphenyl and ditolylether as well as diisopropylbiphenyl mixtures and ditolylether mixtures, in particular technical ditolylether mixtures are preferred. If p or q signify 2 the two alkyl radicals may have different significances or preferably the same significance and may be in any two positions of the phenyl radical (2,3; 2,4; 2,5; 2,6; 3,4; 3,5); particularly worth mention are the corresponding dixylylethers and dixylylether mixtures, in particular technical dixylylether mixtures. Also the mixed ethers are worth mention, in particular phenyl-tolyl-ether, phenyl-xylyl-ether and tolyl-xylyl-ether. Of the mentioned compounds of formula (II) those with p=0 or 1 and q=0 or 1 are preferred, principally biphenyl, isopropylbiphenyl, diphenylether and, in particular, ditolylether.

The sulphonation of the compounds of formulae (I) and (II) may take place under conventional sulphonation conditions, preferably employing oleum, 100% sulphuric acid, concentrated sulphuric acid or chlorosulphonic acid. The sulphonation may be carried out advantageously in the temperature range of from room temperature (=20° C.) to 150° C., preferably 70°–135° C. In the—particularly preferred—sulphonation with 100% or concentrated sulphuric acid, the conditions may, if desired, be chosen so that the reaction-water is eliminated (e.g. distilled or evaporated, optionally under reduced pressure). The sulphonation is suitably carried out under such conditions, that per molecule of formula (I) and/or (II) there are introduced on average 0.7 to 2, advantageously 0.8 to 1.5, preferably 0.8 to 1.2 sulpho groups, advantageously by employing 0.9 to 2.5 moles, preferably 1.0 to 1.8 moles of the sulphonation agent per mole of starting material of formula (I) or (II) or of the mixture of the starting materials of formulae (I) and (II). In the preferred sulphonation with 100% or concentrated sulphuric acid (i.e. in particular $H_2SO_4 \cdot H_2O$ to $H_2SO_4$, in other words $H_2SO_4$ containing 1 to 0 molecules of water per molecule) reaction water is advantageously distilled off under reduced pressure by which the continuation of the sulphonation reaction is favoured and contemporarily non-sulphonated starting material may be distilled off and the sulphonation product reaches a sulphonation degree of principally 0.8 to 2, advantageously 0.9 to 1.5, preferably 1.0 to 1.5, among which products with average degree of sulphonation of 1.0 to 1.4 are particularly preferred. An alkylation of naphthalene with alcohols $R_1$—OH and/or $R_2$—OH and/or of biphenyl or diphenyl(thio)ether with alcohols $R_3$—OH and/or $R_4$—OH to corresponding compounds of formula (I) respectively (II) may optionally be carried out together with the sulphonation in the same sulphonation medium.

The sulphonation products (a) may be represented by means of the following average formula

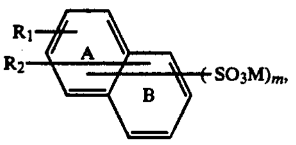

(Ia)

in which m signifies 0.7 to 2 and

M signifies hydrogen or a cation.

The sulphonation products (b) may be represented by the following average formula

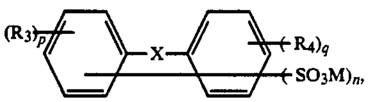

(IIb)

in which n signifies 0.7 to 2.

In formula (Ia) each of the rings A and B contains advantageously not more than one sulpho group. In formula (IIb) each of the benzene rings contains advantageously not more than one sulpho group. The indexes m and n represent the degree of sulphonation indicated above and are advantageously each in the range of 0.8 to 1.5, preferably 0.8 to 1.2. The sulphonation is advantageously carried out so that a degree of sulphonation as unitary as possible is achieved, with m resp. n=0.8 to 1.2 in particular so that at least 50 mole %, preferably at least 80 mole % of the products are monosulphonated, respectively with m resp. n=0.9 to 1.5 or 1.0 to 1.5 so that at least 90 mole % respectively at least 98 mole %, preferably 100% of the products are sulphonated. The compounds of formulae (I) and (II) may be sulphonated separately or with particular advantage also together in one reaction mixture.

After completion of the sulphonation the obtained products [in which in particular in formulae (Ia) and (IIb) M signifies hydrogen] may be converted to a corresponding salt form, preferably M'-salt form, in particular in which in formulae (Ia) and (IIb) M signifies a cation M', by reaction with a suitable base or a salt of a strong base with a weak acid. As cations M' come principally into consideration colourless cations, in particular alkali metal cations (preferably lithium, sodium, potassium), alkaline earth metal cations (preferably magnesium) and/or ammonium cations (preferably unsubstituted ammonium, morpholinium or ammonium substituted with $C_{1-2}$-alkyl and/or $C_{2-3}$-hydroxyalkyl, in particular mono-, di- or triethanolammonium or mono-, di- or triisopropanolammonium) which may be introduced by treatment of the sulphonic acids with corresponding bases or their salts of weak acids, principally with alkali metal hydroxydes, carbonates or bicarbonates, magnesium hydroxide or carbonate, ammonia or corresponding amines. The base or/and the salt of a strong base with a weak acid is added advantageously in such amounts that the pH of an aqueous 10 weight % solution of the products is in the range of 5.5 to 9.0, preferably 7.0 to 8.0.

The products (a) and (b), respectively the compounds of formulae (I) and (II), are advantageously employed in a molar ratio (a)/(b), respectively (I)/(II), in the range of 10:90 to 80:20, preferably 20:80 to 70:30, more preferably 40:60 to 60:40.

The obtained mixtures are—in particular in salt form, preferably M'-salt form—readily soluble in water and may be handled so as produced, optionally after adjusting the water content to a dry substance content of preferably 10–70% by weight or they may, if desired, be dried, e.g. by pulverizing or granulating (optionally with addition of granulating assistants), to give dry compositions.

The compositions (P) may consist only of (a) and (b)—optionally at least in part in salt form—or may contain further additives [e.g. (c) as defined below and/or diluting agents, e.g. water].

A particular embodiment of the invention is represented by compositions ($P_1$) which are characterized by a content of (a) and (b) at least partially in salt form, preferably M'-salt form and are either dry mixtures of (a) and (b) at least partially in salt form or aqueous compositions with a dry substance content [(a)+(b) at least partially in salt form] of 10–70% by weight and which, besides (a) and (b), at least partially in salt form, contain no further additions. As (a) and (b), at least partially in salt form, there are meant corresponding sulphonation products as resulting by sulphonation of the compounds of formulae (I) and (II) and salt formation thereof and may contain optionally corresponding by-products from their production (essentially M'-sulphates and optionally organic by-products as may occur during sulphonation reactions). The pH of an aqueous composition ($P_1$) of 10 weight % content of (a)+(b), at least partially in salt form, being advantageously in the range of 5.5 to 9.0, preferably 7.0 to 8.0.

The above-mentioned mixtures and compositions have levelling, barré-covering, reserving and retarding properties, in particular on nitrogen-containing substrates with high-affinity for anionic dyes, as well as hydrotropic and dispersing properties and favour dye migration. They serve as application assistants for the treatment of fibrous materials in processes that are carried out in aqueous medium. As treatment of fibrous material there is meant here essentially the application of products that modify the aspect and/or the physical properties and/or the colouristic properties of the substrate, mainly the application of dyes, optical brighteners and (for leather substrates) also fat-liquoring agents, (re)-tanning agents and/or fillers. The treatment is carried out "in the presence of" the application assistant in the sense that the assistant is present during at least part of the treatment of the fibrous material with the modifying product by virtue of being applied to the material prior to or after the application of the modifying product thereto or by virtue of the modifying product being applied to the material from an aqueous medium containing the assistant. They serve, in particular, as assistants in the dyeing and/or optical brightening of various fibrous substrates, preferably of textile material [principally of natural, semi-synthetic or fully-synthetic nitrogen-containing fibrous material, in particular natural or synthetic polyamides (e.g. wool, silk, synthetic polyamides), polyurethanes, basically-modified polyalkylenes (polypropylene) or polyacrylonitril] and leather and in the tanning, re-tanning and fat-liquoring of leather. The above-defined compositions (P), in particular ($P_1$), may also be employed as additives in dyestuff preparations, in particular in dry preparations or in concentrated liquid preparations of anionic dyes—e.g. such as defined in the "Colour Index" under the headings Acid Dyes, Reactive Dyes, Mordant Dyes, Leather Dyes, Solubilized Sulphur Dyes and Condense Sulphur Dyes—or further of anionic optical brighteners. Per 100 parts by weight of pure dye or optical brightener there are employed advantageously 2–100, preferably 4–50 parts by weight of [(a)+(b)], preferably at least partially in salt form, as defined above, preferably M'-salt form.

With particular advantage the compositions (P), in particular ($P_1$) are employed as assistants for the dyeing or optical brightening of nitrogen-containing substrates. The compositions (P) act especially as levelling agents and are of particular value for the dyeing of synthetic polyamides and of fibre blends containing besides synthetic polyamide fibres other nitrogen-containing fibres displaying a different affinity for the anionic dye (mainly wool, silk and elastomeric fibres) since the mixtures of (a) and (b) display an optimum retarding and reserving activity on the substrate of higher affinity, so that very equilibrated dyeings of even tone are obtainable. Also in the dyeing of leather there may be achieved very level dyeings. Particularly worth mention is the levelling activity even when using dye-mixtures. The mixtures of (a) and (b) are advantageously employed in the aqueous liquor in a concentration in the range of 0.2 to 10%, preferably 0.5 to 4%, referred to the weight of the substrate. They may be employed as sole levelling agents or may, if desired, also be combined or even blended with (c) further conventional, preferably ($c_1$) anionic, ($c_2$) non-ionic, ($c_3$) weakly cationic or ($c_4$) amphoteric dispersing and/or levelling agents

[weight ratio of the mixture (a)+(b) to (c), advantageously 9:1 to 1:9, preferably 5:5 to 9:1] and a further particular aspect of the invention is represented by compositions ($P_2$) comprising (a), (b) and (c).

Preferred further anion-active assistants ($c_1$) are, in particular, sulpho group-containing compounds, principally lignine sulphonates, fatty sulphonates and condensation products of optionally alkyl substituted sulphonated aromatic compounds with formaldehyde, preferably of naphthalene sulphonic acid and formaldehyde and further sulpho group-containing aromatic mono- and polysulphones, higher molecular fatty alcohol sulphates (in particular sodium dodecylsulphate), mono- or dialkylsulphosuccinate (in particular dioctylsodiumsulphosuccinate) and aliphatic hydrocarbon sulphonates (in particular petroleum sulphonates and secondary $C_{13-17}$-alkylsulphonates); among these the lignine sulphonates and the sulphonated fats (principally sulphonated triglycerides of at least partially unsaturated and/or hydroxy group-containing fatty acids) are preferred.

As non-ionic assistants ($c_2$) of levelling and/or dispersing character that may be employed together with the mixture of (a) and (b) respectively with the compositions (P) there may in particular be mentioned the following: oxyethylation products of higher fatty alcohols, fatty acids or fatty acid amides, of partially esterified polyols, preferably glycerine-, sorbitan- or sorbitol-mono-, sesqui- or -diesters of higher fatty acids, or of triglycerides of higher fatty acids containing at least one hydroxy group.

Weakly cationic assistants ($c_3$) include in particular polyglycolethers of fatty amines or fatty aminoalkylamines.

Amphoteric assistants ($c_4$) include, in particular, the sulphated or carboxymethylated derivatives of the above weakly cationic ones.

The fatty radicals contain preferably 12 to 24 carbon atoms.

In the fatty aminoalkylamine derivatives the alkylene bridge between the two amino groups contains advantageously 2 to 6, preferably 3 carbon atoms.

The degree of oxyethylation is advantageously in the range of 5 to 70 for the non-ionic assistants and advantageously in the range of 20 to 130 for the weakly cationic ones and the amphoteric ones.

The anionic groups in ($c_1$) and ($c_4$) are advantageously in salt form, in particular of cations as described above for M'.

Suitable additives and blending agents may be optimally chosen, depending on the active substance and application method.

Any conventional substrates dyeable with anionic dyes are suitable, principally nitrogen-containing fibrous materials, especially leather or fibrous material made of basically modified polyolefines, polyurethanes or natural or synthetic polyamides, of which before all amide group-containing fibrous material, in particular textile material of natural and/or synthetic polyamides is preferred, mainly wool, silk, Polyamide 6, Polyamide 66, Polyamide 11, Polyamide 46, Qiana and blends thereof with each other or with elastomeric fibres. The substrates may be in any form as conventionally employed for dyeing, in particular from aqueous medium, e.g. as loose fibres, yarns, filaments, hanks, spools, woven or knitted goods, felts, non-wovens, velvet, carpets, tuftings as well as half-ready or ready-made goods. The fibres may also have been treated mechanically and/or thermically, e.g. stretched or texturized, and there may also be employed blends of fibres of different kind or even of different pretreatment (e.g. as suitable for the differential dyeing).

The mentioned substrates may be dyed according to any conventional dyeing methods, in particular by exhaustion methods from aqueous liquor or by impregnation with aqueous compositions (particularly liquors or pastes).

Exhaustion dyeing may take place at conditions conventional per se, for polyamide-containing textile material mainly in the temperature range of 40° to 120° C., optionally with pressure (at normal pressure, advantageously at 60° C. to boiling temperature, with pressure advantageously at 102° to 115° C.) and in the pH range of 3.5 to 10, advantageously 4 to 7. The pH may e.g. be adjusted using conventional acids (e.g. formic acid, acetic acid, tartaric acid or citric acid) or buffers e.g. phosphate, tartrate or acetate buffers (e.g. sodium hydrogen phosphate, ammonium tartrate or sodium acetate/acetic acid). In pH-controlled dyeing processes there may e.g. be started at pH 9–10 and during the dyeing procedure the pH may be lowered to the desired value, e.g. down to 3.5 to 4.5. When using dyes of so-called neutral build-up the pH value is maintained for the dyeing of synthetic polyamides advantageously at relatively weakly acidic to neutral values, principally in the range of 4.5 to 6; for the dyeing of wool similar pH values are preferred, mainly pH-values in the range of 4 to 5.5.

As impregnation methods any conventional methods are suitable by which the substrate is impregnated with an aqueous liquor or paste, e.g. by dipping, padding, pouring on, spraying or printing, after which the dyeing may be fixed by any conventional after-treatment, for textile material advantageously by dwelling in the cold (in particular in the temperature range of 15°-40° C., preferably 20°-30° C.) or by steaming (in particular at 100°-105° C.).

The mixtures and compositions (P), in particular ($P_1$) and ($P_2$) are of particular value as levelling assistants and migration assistants with retarding and also reserving properties which are the more pronounced the higher the affinity of the nitrogen-containing substrates is for the anionic dye, so that also for substrates with different dye-affinity, there are obtainable calm level dyes of even tone. This also if there are employed dye-mixtures as occur e.g. in a dye-gamut or in particular also in trichromatic dyeings. The assistants (P) are in particular also suitable for the subsequent levelling of corresponding unlevel dyeings.

The compositions (P) [especially ($P_1$) and/or ($P_2$)] serve also as assistants in the treatment of leather from aqueous medium in various treatment stages, e.g. in tanning (as tanning assistants), in re-tanning in combination with tanning or re-tanning agents (e.g. vegetable, mineral and/or synthetic tanning agents) or with filling agents or in the fat-liquoring with leather fat-liquoring agents in fat liquor compositions (e.g. with natural, optionally modified fat-liquoring agents and/or with synthetic fat-liquoring agents) and as dyeing assistants before, during or after the dyeing. For this any conventional dyes, preferably hydrosoluble anionic dyes, in particular as mentioned above, are suitable. The mixtures (a)+(b) are employed advantageously in concentrations of 0.2 to 6% by weight, preferably 0.5 to 4% by weight, referred to the wet-weight of the leather. The application on leather may take place advantageously under weakly basic to clearly acidic conditions, preferably at pH-values in the range of 3 to 8, in particular 4 to 6.5, and at conventional leather treatment temperatures, preferably 25° to 75° C.

The compositions (P) [especially ($P_1$) and/or ($P_2$)] are distinguished by their light-fastness and do not favour the formation of foam—in particular in aqueous medium as customary. Aqueous compositions containing the mixtures (a)+(b) are distinguished by their stability and lack of foam, even at high temperatures and strong dynamic stress of the liquors and are hence particularly suitable for all those applications in which the formation of large foam volumes is undesired, thus especially in dyeing processes and finishing processes in which the goods to be treated and the liquor are subject to high dynamic stress, e.g. for the dyeing in jet-dyeing machines, in the winch-beck, in the jigger and in dyeing-drums or for the dyeing of cross-wound bobbins. There are obtainable dyeings of optimum properties.

As disclosed in copending U.S. patent application Ser. No. 07/572,520, now U.S. Pat. No. 5,207,822 the disclosure of which is incorporated herein by reference, mixtures of sulphonation products (a) and (b) of the present invention wherein the sum of the number of carbon atoms in $R_1$ and $R_2$ is at least 2 and X is oxygen and $R_3$ and $R_4$ are preferably ethyl or particularly methyl are also useful as intermediates which can be reacted with formaldehyde to produce condensation products, which, in turn, are useful as dispersants, levelling agents and tanning assistants.

In the following Examples the parts and percentages are by weight, the temperatures are indicated in degrees Celsius; the employed diisopropylnaphthalene is a commercially available isomeric mixture (KMC of RÜTTGER'S-WERKE A. G., Duisburg, Germany) containing the positional isomers 1,3, 1,4, 1,5, 1,6, 1,7, 2,6 and 2,7; the employed dimethylnaphthalene is an analogous commercially available isomeric mixture; the employed methylnaphthalene is a commercially available isomeric mixture of α-methylnaphthalene and β-methylnaphthalene; the ditolylether is a commercially available isomeric mixture containing the positional isomers 2,2', 2,3', 2,4', 3,4' and 4,4' and the isopropylbiphenyl is a commercially available isomeric mixture containing the isomers ortho, meta and para. 1 mm Hg≃1.333 mbar.

EXAMPLE 1

α) 117.6 parts of 100% sulfuric acid are added during 25 minutes at 75° C. under a nitrogen blanket into a mixture of 106 parts of diisopropylnaphthalene and 99 parts of ditolylether, by which the temperature raises to 80°-85° C. The reaction mixture is then heated to 105° C. and stirring is continued until a sample is hydrosoluble, which takes place after about 3 hours. Thereafter the reaction mixture is heated under reduced pressure (30 mm Hg≃40 mbar) to 120° C. and water is distilled off during 1,5 hours and stirring is continued for 1 further hour at 120° C. and 30 mm Hg. After turning off the heating and releasing the vacuum the reaction mixture is cooled to 70° C. and treated with 100 parts of demineralized water during 10 minutes. Then the reaction mixture is cooled to 40° C. and the pH is adjusted to 7.5-8.0 by addition of 95 parts of aqueous 25% ammonia, after which 110 parts of demineralized water are added. There are obtained 610 parts of composition.

β) By evaporation of the 610 parts of solution obtained in above Example 1α) in the ROTAVAPOR there are obtained 374 parts of dry non-crystalline product.

EXAMPLE 2

α) 127.4 parts of 100% sulphuric acid are added during 25 minutes at 75° C. under a nitrogen blanket into a mixture of 106 parts of diisopropylnaphthalene and 99 parts of ditolylether, by which the temperature raises to 80°-85° C. Then the reaction mixture is heated to 108°-110° C. and further stirred until a sample is hydrosoluble, which takes place after about 3 hours. Then the mixture is heated to 120° C. under reduced pressure (40 mbar) and water is distilled off during 1.5 hours, stirring is then continued for 1 further hour at 120° C. and 40 mbar. After turning off the heating and releasing the vacuum the reaction mixture is cooled to 68° C. and treated with 150 parts of demineralized water/ice during 10 minutes. Then the mixture is cooled to 40° C. and treated with 178.5 parts of aqueous 30% NaOH-solution to reach a pH of 7.8. There are obtained 636 parts of composition.

β) By evaporation of the 636 parts of solution obtained in Example 2α) above in a ROTAVAPOR there are obtained 307 parts of dry powdery product.

EXAMPLE 2.1

The procedure of Example 2 is repeated, with the difference, that in place of 178.5 parts of aqueous 30%

NaOH-solution there are added 250.4 parts of aqueous 30% KOH-solution.

EXAMPLE 2.2

Example 2 is repeated with the difference that in place of 178.5 parts of aqueous 30% NaOH-solution there are added 115 parts of aqueous 25% ammonia.

EXAMPLE 2.3

Example 2 is repeated with the difference that in place of 178.5 parts of aqueous 30% NaOH-solution there are added 214.5 parts of an aqueous 30% solution of equimolar proportions of NaOH and KOH.

EXAMPLE 2.4

Example 2 is repeated with the difference that in place of 178.5 parts of aqueous 30% NaOH-solution there are added 57.5 parts of aqueous 25% ammonia and 89.2 parts of aqueous 30% NaOH-solution.

EXAMPLE 2.5

Example 2 is repeated with the difference that in place of 178.5 parts of aqueous 30% NaOH-solution there are added 56.5 parts of 100% $MgCO_3$ and 122 parts of demineralized water.

Analogously as described in the above Examples 1 and 2 there are produced compositions of the invention employing the reactants and molar ratios indicated in the following table.

| Ex. Nr. | Compound of formula (I) (moles) | Compound of formula (II) (moles) | moles of $H_2SO_4$ | Base for salt-formation (pH 7.5-8) |
|---|---|---|---|---|
| 3 | Diisopropyl-naphthalene (0.9) | Ditolylether (0.1) | 1.1 | $NH_4OH$ |
| 4 | Diisopropyl-naphthalene (0.75) | Ditolylether (0.25) | 1.1 | $NH_4OH$ |
| 5 | Diisopropyl-naphthalene (0.6) | Ditolylether (0.4) | 1.25 | $NH_4OH$ |
| 6 | Diisopropyl-naphthalene (0.25) | Ditolylether (0.75) | 1.3 | $NH_4OH$ |
| 7 | Diisopropyl-naphthalene (0.4) | Ditolylether (0.6) | 1.15 | $H_2NCH_2CH_2OH$ |
| 8 | Diisopropyl-naphthalene (0.5) | Diphenyl-ether (0.5) | 1.5 | $NH_4OH$ |
| 9 | Dimethyl-naphthalene (0.4) | Ditolylether (0.6) | 1.15 | $NH_4OH$ |
| 10 | Methyl-naphthalene (0.4) | Ditolylether (0.6) | 1.15 | $NH_4OH$ |
| 11 | Diisopropyl-naphthalene (0.5) | Isopropyl-biphenyl (0.5) | 1.1 | $NH_4OH$ |
| 12 | Diisopropyl-naphthalene (0.8) | Biphenyl (0.2) | 1.3 | $NH_4OH$ |

APPLICATION EXAMPLE A 100 parts of a pre-wetted and previously fixed Polyamide 66/wool mixed fabric are introduced into a dyebath consisting of 400 parts of water, 2 parts of the composition according to Example 1α), 2 parts of acetic acid and 20 parts of anhydrous sodium sulphate at 50° C. and treated for 20 minutes at this temperature in this liquor. Then 0.3 parts of the dye C.I. Acid Red 57 are added, the dyeing liquor is heated during 45 minutes at 96°-98° C. and maintained at this temperature for 1 hour. During the dyeing the evaporated water is continuously replaced. After cooling the dyed fabric is taken out from the liquor, rinsed and dried. There is obtained a level red dyeing.

APPLICATION EXAMPLE B

Application A is repeated with the difference that together with the composition according to Example 1α), the acetic acid and the sodium sulphate, 2 parts of castor oil sulphonate are added to the liquor.

APPLICATION EXAMPLE C (The percentages refer to the dry weight of the substrate.)

A fabric consisting by 20% of Polyamide 66 (NYLSUISSE) and by 80% of wool (woolgabardine) is dyed in conventional way at a liquor-to-goods ratio of 30:1 during 60 minutes at 98° C. The dyeing liquor contains

| | |
|---|---|
| 0.21% | of C.I. Acid Orange 67 |
| 0.07% | of C.I. Acid Red 336 |
| 0.07% | of C.I. Acid Red 118 |
| 0.09% | of C.I. Acid Red 412 |
| 0.03% | of C.I. Acid Blue 80 |
| 0.03% | of C.I. Acid Blue 130 |
| 0.03% | of C.I. Acid green 25 |
| 5% | of GLAUBER's salt, calcined |
| 3.5 g/l | of sodium acetate |
| 2.5 g/l | of glacial acetic acid |
| 4% | of the reserving agent according to Example 1α). |

There is obtained a level-dyed fabric.

APPLICATION EXAMPLE Cbis

The procedure of Application C is repeated, with the difference, that in place of the there employed dye-mixture of C.I. Acid Orange 67, Red 336, Red 118, Red 412, Blue 80, Blue 130 and Green 25 there are employed 1.6% of C.I. Acid Orange 67 and in place of the 4% of the product of Example 1α) there are employed 2.6% thereof.

APPLICATION EXAMPLE D

The procedure of Application Example C is repeated, with the difference, that the liquor further contains 1.5% of the addition product of 105 moles of ethyleneoxide to 1 mole of behenylaminopropylamine or of 100 moles of ethyleneoxide to 1 mole of γ-tallow fatty aminopropylamine.

APPLICATION EXAMPLE E 100 parts of pre-washed Polyamide 66/Spandex mixed fabric are introduced at 40° C. into a liquor consisting of 4000 parts of water, 3 parts of the composition according to Example 1α), 2 parts of acetic acid and 2 parts of castor-oil sulphonate. After a pre-treatment time of 20 minutes, 0.2 parts of the dissolved dye C.I. Acid Blue 129 are added, the dye-liquor is heated in the course of 30 minutes to 90° C. and maintained at this temperature during 1 hour. During the dyeing the evaporated water is continuously replaced. After cooling the blue dyed fabric is taken out from the liquor, rinsed with water and dried. There is obtained a level blue dyeing.

APPLICATION EXAMPLE F

Drum-Dyeing of Leather

Semi-chrome tanned cow-leather of 1.6 mm thickness is set to pH 4.5 to 5.5 in 150% of water with 0.5% of sodium formate and 0.8% of sodium bicarbonate and then the bath is drained-off. For re-tanning there are added 150% of water, 4% of re-tanning agent [poly(-meth)acrylate resin] and 1% of di-(sulphonaphthyl)-methane (dispersion) and re-tanning is carried out during 40 minutes at 35° C.; then the bath is drained-off and there are added 150% of water of 50° C., 1% of the product according to Example 1α) and a dye-mixture of 1% of C.I. Acid Yellow 204 and C.I. Acid Blue 193 and dyeing is carried out during 30 minutes. 5% of fat-liquoring agent (3% of sulphited fish-oil and 2% of sulphated coconut-oil) are then added and treatment is continued for 45 minutes. Then, 1% of formic acid are added for acidification and treatment is continued for 30 minutes. The bath is then drained-off and the leather is washed with 300% of water during 5 minutes at 50° C. The leather is dried hanging and mechanically finished in the usual way. It is regularly dyed in a green shade.

APPLICATION EXAMPLES A1 TO F1

Analogously as the product according to Example 1α), corresponding amounts of the products according to each of Examples 1β), 2 to 2.5 and 3 to 12 are employed in the above Application Examples A, B, C, D, E and F by which the dyes are also well dispersed in the respective liquors and there are obtained level-dyeings.

APPLICATION EXAMPLES A2 TO F2

The product according to Example 2β) may also be admixed dry (e.g. in a ball-mill) in the weight ratio of 1:1, 1:2 or 1:4 with the respective dyes mentioned in Application Examples A, C, E and F and used therein in the form of these mixtures by which the quantity of assistants used in the respective Application Examples may be correspondingly reduced or—in the case of Application Example Cbis, when using the dry mixture assistant/dye in the weight ratio of 1:1—the separate addition of the assistant may be completely omitted. Analogously the assistants of the other Examples may be admixed with the dyes in the weight ratios of 1:1, 1:2 and 1:4 as indicated here above.

I claim:

1. A process for the treatment of fibrous material made of synthetic polyamide or leather which comprises carrying out said treatment from an aqueous medium in the presence of an application assistant which is a composition (P) comprising a mixture of (a) a sulphonation product of a compound of formula

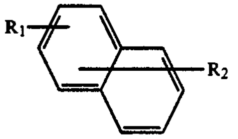

(I)

in which $R_1$ signifies $C_{1-4}$-alkyl and $R_2$ signifies hydrogen or $C_{1-4}$-alkyl, or a mixture of compounds of formula (I) and (b) a sulphonation product of a compound of formula

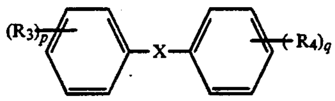

(II)

in which each of $R_3$ and $R_4$, independently, signifies $C_{1-4}$-alkyl, X signifies oxygen, sulphur or the direct bond and each of p and q, independently, signifies 0, 1 or 2, or a mixture of compounds of formula (II)

wherein (a) and (b) have a degree of sulphonation of, on average, 0.8 to 1.2 sulpho groups per molecule of compounds of formulae (I) and II and are optionally at least partially in salt form.

2. A process according to claim 1, wherein each of $R_3$ and $R_4$ signifies methyl and each of p and q signifies 1 or 2.

3. A process according to claim 1, wherein each of $R_1$ and $R_2$ signifies isopropyl.

4. A process according to claim 1, wherein the molar ratio (a)/(b) is in the range of 40:60 to 60:40.

5. A process according to claim 1 in the further presence of (c) at least one conventional dispersing and/or levelling agent.

6. A process according to claim 5, wherein the weight ratio of the mixture (a)+(b) to (c) is 9:1 to 1:9.

7. A process according to claim 1, wherein (a) corresponds to formula

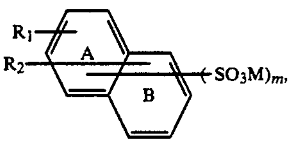

(Ia)

in which

M signifies hydrogen or a cation and m signifies 0.8 to 1.2, and (b) corresponds to formula

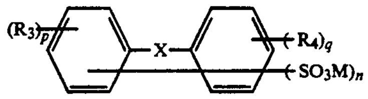

(IIb)

in which n signifies 0.8 to 1.2 and the molar ratio (a):(b) is in the range 20:80 to 70:30.

8. A process according to claim 3 wherein, in formulae (Ia) and (IIb), $R_2$ is $C_{1-4}$ alkyl, the total number of carbon atoms in $R_1+R_2$ is at least 4, X is a direct bond or oxygen, p is 0 or 1 and q is 0 or 1.

9. A process according to claim 8 wherein, in formulae (Ia) and (IIb), M is M' where M' is a cation selected from the group consisting of alkali metal, alkaline earth metal and ammonium cations.

10. A process according to claim 8 which comprises applying to the fibrous material a modifying product selected from dyes, optical brighteners and, where the fibrous material is leather, fat liquoring agents, tanning agents, retanning agents and fillers, said modifying product being applied before or after application of composition (P) to the material or from an aqueous medium containing composition (P).

11. A process according to claim 3 which comprises applying to the fibrous material a modifying product selected from dyes, optical brighteners and, in the case of leather, fat liquoring agents, tanning agents, retanning agents and fillers, said modifying product being applied before or after application of composition (P) to the fibrous material or from an aqueous medium containing composition (P).

12. A process according to claim 11 wherein composition (P) is a composition ($P_1$) comprising, at least partially, compounds of formulae (Ia) and (IIb) wherein M is M' where M' is a cation selected from the group consisting of alkali metal, alkaline earth metal and ammonium cations, the fibrous material is synthetic polyamide or a blend of synthetic polyamide with wool, silk or nitrogen-containing elastomeric fibers and the modifying product is an anionic dye.

13. A process according to claim 11 wherein (b) is a sulphonation product of biphenyl, isopropylbiphenyl, diphenyl ether or ditolyl ether.

14. A process according to claim 1, wherein the treatment is the dyeing or optically brightening of textile material or the tanning or re-tanning, dyeing or fat-liquoring of leather.

15. A process according to claim 9 wherein the dyeing is a dyeing with anionic dyes.

16. A process according to claim 14 wherein the treatment is dyeing.

17. A process according to claim 16 wherein the treatment is the dyeing of textile material comprising synthetic polyamides.

18. A process according to claim 17 wherein the treatment is the dyeing of a mixture of synthetic polyamide fibers with wool and/or with silk and/or with nitrogen-containing elastomeric fibers.

19. A process according to claim 12, wherein the dyeing is effected with anionic dyes suitable for the dyeing of synthetic polyamides.

20. A process according to claim 19 wherein the treatment is the dyeing of a mixture of synthetic polyamide fibers with wool.

21. A composition (P) comprising a mixture of (a) a sulphonation product of a compound of formula

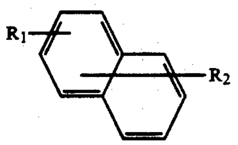

(I)

in which $R_1$ signifies $C_{1-4}$-alkyl and $R_2$ signifies hydrogen or $C_{1-4}$-alkyl, or a mixture of compounds of formula (I) and (b) a sulphonation product of a compound of formula

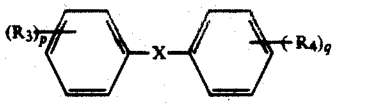

(II)

in which each of $R_3$ and $R_4$, independently, signifies $C_{1-4}$-alkyl, X signifies oxygen, sulphur or the direct bond and each of p and q, independently, signifies 0, 1, or 2, or a mixture of compounds of formula (II), the degree of sulphonation in (a) and (b) being, on average, 0.8 to 1.2, optionally at least partially in salt form.

22. A composition (P) according to claim 21 wherein (a) corresponds to formula

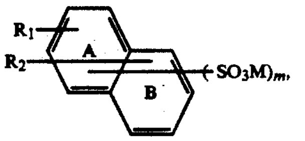

(Ia)

in which

M signifies hydrogen or a cation and m signifies 0.8 to 1.2, and (b) corresponds to formula

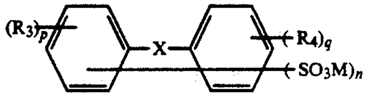

(IIb)

in which n signifies 0.8 to 1.2 and the molar ratio (a)/(b) is in the range 20:80 to 70:30.

23. A composition (P), according to claim 22 wherein, in formulae (Ia) and (IIb), $R_2$ is $C_{1-4}$ alkyl, the total number of carbon atoms in $R_1+R_2$ is at least 4, X is a direct bond or oxygen, p is 0 or 1 and q is 0 or 1.

24. A composition (P) according to claim 23 wherein, in formulae (Ia) and (IIb), M is M' where M' is a cation selected from the group consisting of alkali metal, alkaline earth metal and ammonium cations.

25. A composition according to claim 21 wherein (b) is a sulphonation product of biphenyl, isopropylbiphenyl, diphenyl ether or ditolyl ether.

26. A composition (P) according to claim 21 which is a composition ($P_1$) wherein (a) and (b) are at least partially in salt form, and which is either a dry mixture of (a) and (b) or an aqueous composition having a dry substance content of (a)+(b) of 10 to 70% by weight.

27. A process for the production of a composition ($P_1$) according to claim 26 which comprises sulphonating a corresponding mixture of compounds of formulae (I) and (II) and at least partially converting the resulting product to a salt form.

28. A process for the treatment of fibrous material of synthetic polyamide or leather from aqueous medium in the presence of an application assistant, wherein the application assistant is a composition ($P_1$) according to claim 26.

29. A dry dye composition comprising at least one anionic dye and a dry mixture ($P_1$) as defined in claim 26.

30. A composition comprising at least one anionic dye or optical brightener and (P) as defined in claim 21.

31. A process for the production of a composition (P) according to claim 21 which comprises sulphonating a corresponding mixture of compounds of formulae (I) and (II) to an average degree of sulphonation of 0.8 to 1.2 and optionally converting the resulting product to a salt form.

32. A composition according to claim 21 wherein the compound of formula (II) is ditolylether.

33. A composition (P) according to claim 21 which is a composition ($P_2$) comprising (a) and (b) further in combination with (c) at least one conventional dispersing and/or leveling agent.

34. A process for the treatment of fibrous material of synthetic polyamide or leather from aqueous medium in the presence of an application assistant, wherein the application assistant is a composition ($P_2$) according to claim 33.

35. A composition ($P_2$) according to claim 33 wherein (c) is anionic, non-ionic, weakly cationic or amphoteric and the weight ratio of [(a)+(b)]to (c) is 9:1 to 1:9.

* * * * *